United States Patent

Emig et al.

[11] Patent Number: 5,508,448
[45] Date of Patent: Apr. 16, 1996

[54] PROCESS FOR THE PREPARATION OF TRIOXANE

[75] Inventors: Gerhard Emig, Erlangen; Benno Krüger, Waldems-Esch; Frank Kern, Kandel; Michael Hoffmockel, Niedernhausen; Karl-Friedrich Mück; Günter Sextro, both of Wiesbaden, all of Germany

[73] Assignee: Hoechst Aktiengesellschaft, Germany

[21] Appl. No.: 176,105

[22] Filed: Dec. 30, 1993

[30] Foreign Application Priority Data

Dec. 31, 1992 [DE] Germany .............. 42 44 582.5
Nov. 5, 1993 [DE] Germany .............. 43 37 706.8

[51] Int. Cl.⁶ ................................................. C07D 373/06
[52] U.S. Cl. ................................................. 549/368
[58] Field of Search ................................................. 549/368

[56] References Cited

U.S. PATENT DOCUMENTS 3,496,192  2/1970  Ackermann et al. ............ 549/368
4,381,397  4/1983  Yoshida et al. ............ 549/368
4,563,536  1/1986  Yoshida et al. ............ 549/368

FOREIGN PATENT DOCUMENTS 1526132  4/1966  France .
3106476  12/1981  Germany .
1045639  10/1967  United Kingdom .

*Primary Examiner*—C. Warren Ivy
*Assistant Examiner*—Raymond Covington
*Attorney, Agent, or Firm*—Connolly & Hutz

[57] ABSTRACT

A process for the catalytic preparation of trioxane from formaldehyde in the gas phase employs a catalyst comprising vanadyl hydrogenphosphate hemihydrate which may be unactivated or activated by steam.

No byproducts were obtained in the process and the space-time yield is high. Deposits in the reactor do not occur.

20 Claims, 1 Drawing Sheet

PROCESS FOR THE PREPARATION OF TRIOXANE

The invention relates to a process for the continuous preparation of trioxane in the gas phase by heterogenous catalysis using vanadyl hydrogenphosphate hemihydrate (VO)HPO$_4$·½H$_2$O as catalyst. In one variation of the process, the catalyst is activated by treatment with steam prior to being employed.

Trioxane can be prepared from aqueous formaldehyde solutions using acid catalysts. A characteristic of these processes is the high energy consumption for vaporizing water which is introduced into the process by the feedstock streams. There are various proposals for preparing trioxane from formaldehyde by gas-phase trimerization, but these all use formaldehyde streams containing varying amounts of water. Use of water-containing formaldehyde results in problems caused by deposits of polyoxymethylene on the catalyst surface. A process for preparing trioxane by means of an acid ion-exchange resin is known (DE-C-1 593 990). Likewise known is a gas-phase trimerization catalyst in the form of phosphoric acid and sulfuric acid on SiO$_2$ supports (AT-B 252 913).

The object of the invention was to overcome said disadvantages.

This object is achieved by a process which is distinguished from the prior processes by the catalyst, the composition of the feedstock stream and the high selectivity of the catalyst, particularly at high formaldehyde partial pressures.

Thus, the invention describes a process for the preparation of trioxane from formaldehyde in the gas phase in the presence of vanadyl hydrogenphosphate hemihydrate as catalyst. In a particular embodiment, the catalyst is activated by treatment with steam prior to being employed.

The following advantages warrant particular emphasis:
1. Substantial increase in space-time yields (STY) [kg/m$^3$·h], particularly when the catalyst is activated beforehand with steam.
2. No byproducts
3. Moderate generation of heat in the synthesis reactor.

BRIEF DESCRIPTION OF THE DRAWING

The sole Figure (FIG. 1) of the Drawing is a schematic representation of an apparatus for preparing trioxane in accordance with the process of this invention.

DETAILED DESCRIPTION

Figure 1:
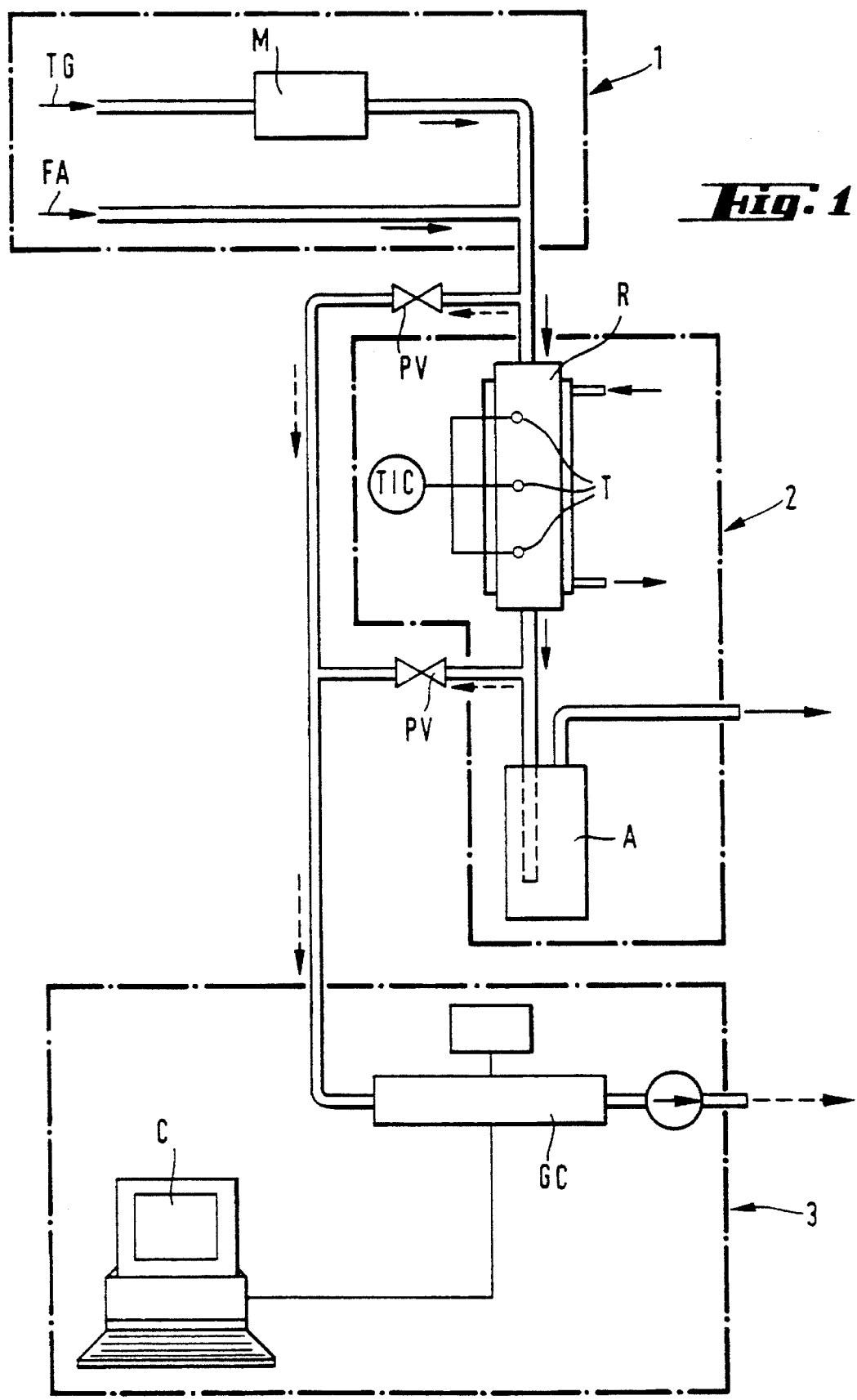

The catalyst is generally employed in pure form, i.e. without supports or pressing aids. Its empirical formula is (VO)HPO$_4$·½H$_2$O. A loss of water under the reaction conditions and the formation of various metaphosphates through to vanadyl pyrophosphate, (VO)$_2$P$_2$O$_7$, i.e. forms of the compound with lower water content, does not alter the activity and selectivity. A substantial increase in activity is achieved by prior treatment of the catalyst with steam at from 100° to 220° C. If in the course of use in a continuous process a reduction in the activity of the catalyst is determined, this can be reversed by steam treatment.

Deposits, such as are usual when phosphoric acid on SiO$_2$ is used, can be prevented by use of the pure catalyst.

The activation is generally carried out at temperatures from 100° to 220° C., preferably from 145° to 200° C., in particular from 165° to 195° C., over a period from 24 hours to 14 days. Lower temperatures and short treatment times do not activate the catalyst. Higher temperatures lead to decomposition of the catalyst. The duration of the treatment can be practically unlimited, but generally an economically justifiable time should be allowed. The time is also dependent on the physical amount of catalyst. For small amounts of catalyst, for example on an experimental scale, the time may be less than 24 hours. It is to be determined in accordance with the individual case.

Activation is carried out with steam which may, if desired, be admixed with a carrier gas. The process is generally carried out without pressure, but increased pressure can also be applied.

The formaldehyde which can be employed for the process may be of different water content, i.e. may contain up to 5% by weight of water. Anhydrous formaldehyde is preferred.

The temperature range for the reaction is from 80° to 150° C. The preferred range is from 100° to 120° C.

The reaction is affected by the partial pressure of the formaldehyde. The catalyst has a high selectivity for the formation of trioxane over a wide pressure range. The partial pressure of the formaldehyde at the inlet is generally from 0.5 to 5 bar, preferably from 0.5 to 2 bar.

The apparatus for preparing trioxane in accordance with the invention comprised three parts (see FIG. 1):
1. Metering
2. Formation reactor
3. Analysis For carrying out a test, formaldehyde (FA) (=feedstock stream) is introduced into the apparatus and, if desired, mixed with a carrier gas (CG). Suitable carrier gases are the noble gases helium, argon, krypton or xenon, but nitrogen is preferred.

The formation reactor (R) comprised, for the present experiments, a stainless-steel tube reactor having a length of 150 mm and a diameter of 30 mm. Heat supply and removal was via a thermostat (TIC), the heat transfer medium was silicone oil. The use of heat transfer media such as mineral oils is likewise possible. The temperature in the reactor was measured radially at three different points (T) along the reactor. These temperatures were recorded during the tests and gave information about the stable operating state of the reactor over the duration of the test. The output stream leaving the reactor and containing the reaction products formed was trapped in water in an absorption device (A). The trioxane formed can be isolated therefrom by extraction in a known manner.

The quantitative tests for the formation of trioxane in the gas phase were carried out with on-line analysis. Samples were taken during operation at two different points on the apparatus and analyzed in a gas chromatograph (GC). The arrangement of the apparatus for the process of the invention and its dimensions can naturally be adapted to the prevailing conditions.

Test Description

Individual parameters which were varied are explained in the individual examples.

Anhydrous formaldehyde was employed in the trimerization tests. A carrier gas (TG), preferably nitrogen, can be added to the feedstock stream (FA) by means of a mass flow regulator (M). However, it is also possible to work without carrier gas. The flow rate of the feedstock stream can be varied, e.g. increased, by use of a carrier gas so as to modify, e.g. lower, the residence time in the reactor (R). The catalyst is, for example, poured into the reactor in the form of pellets, various amounts being employed, as indicated in the examples. Upstream and downstream of the reactor (R), the gas composition was determined on-line by means of a gas chromatograph. The conversion was calculated from the compositions of the gases. The temperature was regulated via a thermostat (TIC) and measured at three different points (T) along the catalyst bed.

Sampling for analysis of the inlet and outlet streams was carried out automatically and at regular intervals, for example every seven minutes, the isolation devices (PV= pneumatic ball valves) being connected to a gas chromatograph (GC) which is controlled via a computer (C).

Yield and conversion in the process of the invention can be determined according to various equations. Thus, for example, the mole fraction $X_{form}$ is based on the gas composition at the inlet of the synthesis reactor. It is calculated according to equation (1).

$$X_{form} = n_{form}^0 / n_{tot} = n_{form} / (n_{form}^0 + n_{N2}) \quad (1)$$

$n_{form}^0$: formaldehyde flow rate at inlet [mol/h]
$n_{tot}$: total flow rate [mol/h]
$n_{N2}$: nitrogen flow rate [mol/h]

The experimentally determined conversion $C_{exp}$ is calculated according to equation (2).

$$C_{exp} = (n_{form}^0 - n_{form}) / n_{form}^0 \cdot 100 \quad (2)$$

$n_{form}^0$: formaldehyde flow rate at inlet [mol/h]
$n_{form}$: formaldehyde flow rate at outlet [mol/h]

The relative conversion $C_{rel}$ (equation (3)) is the ratio of the experimentally determined conversion $C_{exp}$ and the equilibrium conversion $C_{eq}$ determined from the equilibrium constants according to Busfield and Merigold ("The Gas-Phase Equilibrium between Trioxane and Formaldehyde", J. Chem. Soc (A), 1969 p. 2975).

$$C_{rel} = C_{exp} / C_{eq} \cdot 100 \quad (3)$$

$C_{exp}$: experimental conversion [%]
$C_{eq}$: equilibrium conversion [%]

The values in the tables in the examples were obtained from these equations.

EXAMPLES 1) 82 g of the catalyst vanadyl hydrogenphosphate hemihydrate in the form of cylindrical pellets (diameter 5 mm, length 5 mm) were employed in the reactor (R). The temperature of the reactor was 80° C. The following conversions could be achieved at a selectivity of 1, i.e. no byproducts were obtained. The nitrogen flow was 1.8 mol/h.

TABLE 1

| Conversions with various formaldehyde mole fractions at the inlet and a temperature of 80° C. | | | | | | |
|---|---|---|---|---|---|---|
| Temp. [°C.] | Residence time [s] | $n_{form}^0$ [mol/h] | Mole fraction | $C_{exp}$ [%] | $C_{rel}$ [%] | STY [kg/m³h] |
| 80 | 5.82 | 0.43 | 0.193 | 22.1 | 62.8 | 35.3 |
| 80 | 5.93 | 0.39 | 0.178 | 18.7 | 56.6 | 27.1 |
| 80 | 5.97 | 0.38 | 0.173 | 15.8 | 49.0 | 22.2 |
| 80 | 6.0 | 0.37 | 0.169 | 15.4 | 48.7 | 21.0 |

2) Example 1 was repeated at a reactor temperature of 90° C. The following conversions could be achieved at a selectivity of 1. The nitrogen flow rate was 1.8 mol/h.

TABLE 2

| Conversions with various formaldehyde mole fractions at the inlet and a temperature of 90° C. | | | | | | |
|---|---|---|---|---|---|---|
| Temp. [°C.] | Residence time [s] | $n_{form}^0$ [mol/h] | Mole fraction | $C_{exp}$ [%] | $C_{rel}$ [%] | STY [kg/m³h] |
| 90 | 5.40 | 0.52 | 0.225 | 18.0 | 81.3 | 36.3 |
| 90 | 5.85 | 0.34 | 0.160 | 16.2 | 100 | 21.5 |
| 90 | 5.90 | 0.33 | 0.153 | 15.7 | 100 | 19.7 |
| 90 | 6.11 | 0.25 | 0.123 | 13.4 | 100 | 13.0 |

It can be seen that equilibrium conversion can be achieved at increased temperature. The selectivity is maintained on increasing the temperature.

3) 64 g of the catalyst vanadyl hydrogenphosphate hemihydrate in the form of cylindrical pellets (diameter 5 mm, length 5 mm) were employed in the reactor (R). The temperature of the reactor was 110° C. The following conversions could be achieved at a selectivity of 1. The nitrogen flow rate was 0.1–0.2 mol/h. The total pressure was 1700 mbar and the partial pressure of formaldehyde at the inlet was kept constant at 1100 mbar.

TABLE 3

| Conversions with various formaldehyde mole fractions at the inlet and a temperature of 110° C. | | | | | | |
|---|---|---|---|---|---|---|
| Temp. [°C.] | Residence time [s] | $n_{form}^0$ [mol/h] | Mole fraction | $C_{exp}$ [%] | $C_{rel}$ [%] | STY [kg/m³h] |
| 110 | 25.4 | 0.34 | 0.717 | 23.5 | 71.3 | 31.9 |
| 110 | 34.8 | 0.25 | 0.711 | 23.7 | 73.9 | 23.3 |
| 110 | 20.8 | 0.41 | 0.695 | 17.9 | 58.0 | 29.4 |

4) Example 3 was repeated using 21.5 g of catalyst. Reduction in the mass of catalyst caused a shortening of the residence time in the reactor. The total pressure was 1350 mbar, the partial pressure of formaldehyde at the inlet was 900 mbar.

TABLE 4

| Conversions with various formaldehyde mole fractions at the inlet and a temperature of 110° C. | | | | | | |
|---|---|---|---|---|---|---|
| Temp. [°C.] | Residence time [s] | $n_{form}^0$ [mol/h] | Mole fraction | $C_{exp}$ [%] | $C_{rel}$ [%] | STY [kg/m³h] |
| 110 | 6.7 | 0.47 | 0.778 | 6.2 | 25.4 | 35.1 |
| 110 | 7.9 | 0.34 | 0.673 | 7.8 | 33.1 | 32.0 |
| 110 | 8.3 | 0.29 | 0.588 | 9.9 | 39.8 | 33.8 |

5) Example 3 was repeated using a total pressure of 1350 mbar and a partial pressure of formaldehyde at the inlet of 900 mbar.

TABLE 5

| Conversions with various formaldehyde mole fractions at the inlet and a temperature of 110° C. | | | | | | |
|---|---|---|---|---|---|---|
| Temp. [°C.] | Residence time [s] | $n_{form}^0$ [mol/h] | Mole fraction | $C_{exp}$ [%] | $C_{rel}$ [%] | STY [kg/m³h] |
| 110 | 14.9 | 0.61 | 0.752 | 11.6 | 45.5 | 28.4 |
| 110 | 17.9 | 0.50 | 0.751 | 14.8 | 56.5 | 29.8 |
| 110 | 24.1 | 0.37 | 0.732 | 17.8 | 66.3 | 26.1 |
| 110 | 33.0 | 0.26 | 0.725 | 20.4 | 79.5 | 21.6 |

The Examples 1 to 5 show that the catalyst possesses high selectivity for the formation of trioxane. The highest relative conversions can be achieved at a temperature of 90° C., Example 2. However, only low partial pressures of formaldehyde are then possible. From a temperature of 105° C., the partial pressure of formaldehyde can be increased to above 1 bar, Example 3. It can be seen that at longer residence times, for example 33.0 seconds, a relative conversion of up to 79.5%, Example 5, can be achieved. However, in this case the space-time yield is reduced. Optimization of residence time and the partial pressure of formaldehyde, however, allows space-time yields of over 30 kg/m$^3$.h to be achieved (Example 3: residence time 25.4 seconds, partial pressure of formaldehyde 1100 mbar, space-time yield 31.9 kg/m$^3$.h). Lowering the residence time, Example 4, to from 7 to 8 seconds does increase the space-time yield, but the relative conversion is considerably reduced.

Activation of vanadyl hydrogenphosphate hemihydrate: 150 g of freshly prepared vanadyl hydrogenphosphate hemihydrate (particle size from 1 to 2 mm, bulk density 0.63 g/cm$^3$) were placed in a tube reactor (diameter 50 mm, length 150 mm) heated to 180° C. by means of an electric heating sleeve. To activate the catalyst, a gas stream comprising 90 mol % of steam and 10 mol % of nitrogen was passed over the catalyst bed for 3 days at a total pressure of 1100 mbar and a total inlet flow rate of 2.57 mol/h.

Determination of the activity of steam-treated or unactivated vanadyl hydrogenphosphate hemihydrate:

A bed of 20 cm$^3$ of vanadyl hydrogenphospate hemihydrate (particle size from 1 to 2 mm) (corresponding to 12.5 g of fresh or of steam-activated vanadyl hydrogenphosphate hemihydrate) was introduced into a tube reactor made of stainless steel (diameter 30 mm, wall temperature 107.5° C.) and a gas stream comprising 0.2 mol/h of nitrogen and 0.6 mol/h of anhydrous formaldehyde was passed over the bed. The total pressure in the reactor was 1460 mbar and the partial pressure of the formaldehyde at the inlet was 1100 mbar. Gas chromatographic analysis was used to determine the composition of the product obtained which comprised nitrogen, unreacted formaldehyde and the desired reaction product trioxane.

The results of the catalyst activation are summarized below:

6) activated vanadyl hydrogenphosphate hemihydrate: test conditions as described above.

Conversion of formaldehyde to trioxane: 12.5%

Space-time yield of trioxane: 114 kg/m$^3$.h 7) (Comparison): fresh unactivated vanadyl hydrogenphosphate hemihydrate: test conditions as described above.

Conversion of formaldehyde to trioxane: 2.9%

Space-time yield of trioxane: 26 kg/m$^3$.h

As shown by the results, the activity of the vanadyl hydrogenphosphate hemihydrate under identical test conditions is greatly increased by steam treatment.

We claim:

1. A process for the preparation of trioxane from formaldehyde in the gas phase, which process comprises: contacting the formaldehyde in the gas phase with a solid catalyst comprising vanadyl hydrogenphosphate hemihydrate.

2. The process as claimed in claim 1, wherein the water content of the catalyst has been reduced prior to its use in the process.

3. A process for the preparation of trioxane from formaldehyde in the gas phase, which process comprises: treating solid, particulate vanadyl hydrogenphosphate hemihydrate with steam to activate it, and contacting the formaldehyde in the gas phase with the thus-activated solid, particulate vanadyl hydrogenphosphate hemihydrate, employed as a catalyst for converting the formaldehyde to trioxane.

4. The process as claimed in claim 3, wherein the vanadyl hydrogenphosphate hemihydrate is treated at from 100° to 220° C. with steam in the presence or absence of a carrier gas for from 6 hours to 14 days, and the treatment is carried out without pressure or with application of increased pressure.

5. The process as claimed in claim 1, wherein the formaldehyde from which the trioxane is prepared is essentially anhydrous.

6. The process as claimed in claim 3, wherein the formaldehyde from which the trioxane is prepared is essentially anhydrous.

7. The process as claimed in claim 1, wherein the preparation of the trioxane is carried out at from 80° to 150° C.

8. The process as claimed in claim 3, wherein the preparation of the trioxane is carried out at from 80° to 150° C.

9. The process as claimed in claim 1, wherein the preparation of the trioxane is carried out at from 100° to 120° C.

10. The process as claimed in claim 3, wherein the preparation of the trioxane is carried out at from 100° to 120° C.

11. The process as claimed in claim 1, wherein the preparation of the trioxane is carried out in a reactor having an inlet for the formaldehyde, and the partial pressure of the formaldehyde at the inlet is from 0.5 to 5 bar.

12. The process as claimed in claim 3, wherein the preparation of the trioxane is carried out in a reactor having an inlet for the formaldehyde, and the partial pressure of the formaldehyde at the inlet is from 0.5 to 5 bar.

13. The process as claimed in claim 11, wherein the partial pressure of the formaldehyde at the inlet is from 0.5 to 2 bar.

14. The process as claimed in claim 12, wherein the partial pressure of the formaldehyde at the inlet is from 0.5 to 2 bar.

15. The process as claimed in claim 1, wherein the preparation of the trioxane is carried out in the presence of a carrier gas.

16. The process as claimed in claim 3, wherein the preparation of the trioxane is carried out in the presence of a carrier gas.

17. The process as claimed in claim 15, wherein the carrier gas comprises nitrogen.

18. The process as claimed in claim 16, wherein the carrier gas comprises nitrogen.

19. The process as claimed in claim 1, wherein the preparation of the trioxane is carried out in a reactor having an inlet for the formaldehyde and an outlet for a product stream, and wherein the trioxane is recovered from the product stream in a recovery zone external to the reactor.

20. The process as claimed in claim 3, wherein the preparation of the trioxane is carried out in a reactor having an inlet for the formaldehyde and an outlet for a product stream, and wherein the trioxane is recovered from the product stream in a recovery zone external to the reactor.

* * * * *